United States Patent
Dunkel et al.

(10) Patent No.: US 7,598,389 B2
(45) Date of Patent: Oct. 6, 2009

(54) SILYLATED CARBOXAMIDES

(75) Inventors: Ralf Dunkel, Lyons (FR); Hans-Ludwig Elbe, Wuppertal (DE); Benoit Hartmann, Langenfeld (DE); Alexander Klausener, Pulheim (DE); Jörg Nico Greul, Leichlingen (DE); Ulrike Wachendorff-Neumann, Neuwied (DE); Peter Dahmen, Neuss (DE); Karl-Heinz Kuck, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/579,033

(22) PCT Filed: Nov. 6, 2004

(86) PCT No.: PCT/EP2004/012590

§ 371 (c)(1),
(2), (4) Date: Jan. 22, 2007

(87) PCT Pub. No.: WO2005/049624

PCT Pub. Date: Jun. 2, 2005

(65) Prior Publication Data

US 2007/0191454 A1 Aug. 16, 2007

(30) Foreign Application Priority Data

Nov. 21, 2003 (DE) ................. 103 54 607

(51) Int. Cl.
- C07D 231/00 (2006.01)
- C07D 233/00 (2006.01)
- C07D 235/00 (2006.01)
- C07D 249/00 (2006.01)
- C07D 261/00 (2006.01)
- C07D 263/00 (2006.01)
- C07D 271/00 (2006.01)
- C07D 273/00 (2006.01)
- C07D 275/00 (2006.01)
- C07D 277/00 (2006.01)
- C07D 283/00 (2006.01)
- C07D 291/00 (2006.01)
- C07D 293/00 (2006.01)
- C07D 413/00 (2006.01)
- C07D 417/00 (2006.01)
- C07D 419/00 (2006.01)
- C07D 421/00 (2006.01)
- C07D 498/00 (2006.01)
- C07D 513/00 (2006.01)
- C07D 515/00 (2006.01)
- C07D 517/00 (2006.01)
- C07F 5/02 (2006.01)
- C07F 7/02 (2006.01)

(52) U.S. Cl. .................. 548/110; 548/356.1; 548/373.1

(58) Field of Classification Search .............. None
See application file for complete search history.

(56) References Cited

U.S. PATENT DOCUMENTS

| | | | |
|---|---|---|---|
| 5,223,526 A | 6/1993 | McLoughlin et al. |
| 5,330,995 A | 7/1994 | Eicken et al. |
| 5,416,103 A | 5/1995 | Eicken et al. |
| 5,438,070 A | 8/1995 | Eicken et al. |
| 5,486,621 A | 1/1996 | Phillion et al. |
| 5,922,732 A | 7/1999 | Urch et al. |
| 7,176,228 B2 | 2/2007 | Elbe et al. |
| 7,208,169 B2 | 4/2007 | Dunkel et al. |
| 7,314,958 B2 | 1/2008 | Elbe et al. |
| 2001/0046975 A1 | 11/2001 | Phillion et al. |
| 2002/0061913 A1 | 5/2002 | Urch et al. |
| 2002/0119982 A1 | 8/2002 | Wang et al. |
| 2004/0204470 A1 | 10/2004 | Elbe et al. |
| 2005/0182107 A1 | 8/2005 | Ehrenfreund et al. |
| 2006/0154967 A1 | 7/2006 | Ehrenfreund et al. |
| 2007/0191454 A1 | 8/2007 | Dunkel et al. |
| 2007/0203148 A1 | 8/2007 | Dunkel et al. |
| 2007/0293455 A1 | 12/2007 | Dunkel et al. |
| 2008/0064874 A1 | 3/2008 | Dunkel et al. |
| 2008/0085924 A1 | 4/2008 | Dunkel et al. |
| 2009/0076113 A1 | 3/2009 | Dunkel et al. |

FOREIGN PATENT DOCUMENTS

| | | |
|---|---|---|
| DE | 103 25 439 A1 | 12/2004 |
| EP | 0 538 231 A1 | 4/1993 |
| EP | 0 545 099 A2 | 6/1993 |
| EP | 0 589 301 A1 | 3/1994 |
| EP | 0 589 313 A1 | 3/1994 |

(Continued)

OTHER PUBLICATIONS

Silverman. R.B., "The Organic Chemistry of Drug Design and Drug Action", 1992, Academic Press Inc., p. 16.*

(Continued)

*Primary Examiner*—Daniel M Sullivan
*Assistant Examiner*—Yevegeny Valenrod
(74) *Attorney, Agent, or Firm*—Sterne, Kessler, Goldstein & Fox P.L.L.C.

(57) ABSTRACT

Novel silylated carboxamides of the formula (I)

in which
R, L, $R^1$, $R^2$, $R^3$, $R^4$ and A are as defined in the description, a plurality of processes for preparing these compounds and their use for controlling unwanted microorganisms.

15 Claims, No Drawings

FOREIGN PATENT DOCUMENTS

| WO | WO 93/11117 A1 | 6/1993 |
|---|---|---|
| WO | WO 96/37494 A1 | 11/1996 |
| WO | WO 98/25923 A1 | 6/1998 |
| WO | WO 02/08197 A1 | 1/2002 |
| WO | WO 03/010149 A1 | 2/2003 |
| WO | WO 03/080628 A1 | 10/2003 |
| WO | WO 2004/005242 A1 | 1/2004 |
| WO | WO 2004/099195 A1 | 11/2004 |
| WO | WO 2005/004606 A2 | 1/2005 |

OTHER PUBLICATIONS

Abbiati, G., et al., "An Efficient Synthesis of 2,4-Substituted [1,8]Naphthyridines from 3-(2-Amino-5-methylpyridin-3-yl)-1-arylprop-2-yn-1-ones," *Synthesis 13*:1912-1916, Georg Thieme Verlag Stuttgart (2002).

Jóźwiak, A., et al., "Behaviour of N-Pyridylbenzamides versus Benzanilides in the *ortho*-Directed Lithiation of Masked Aromatic Carboxylic Acids," *Eur. J. Org. Chem. 2004*:3254-3261, Wiley-VCH Verlag GmbH & Co. KGaA (2004).

Sakamoto, T., et al., "Condensed Heteroaromatic Ring Systems. XII. Synthesis of Indole Derivatives from Ethyl 2-Bromocarbanilates," *Chem. Pharm. Bull. 35*:1823-1828, Pharmaceutical Society of Japan (1987).

Venuti, M.C., et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-*b*]quinazoline," *J. Med. Chem. 31*:2136-2145, American Chemical Society (1988).

Xu, L., et al., "Transition Metal Catalyzed Synthesis of 5-Azaindoles," *Tetrahedron Lett. 39*:5159-5162, Elsevier Science Ltd. (1998).

International Search Report for International Application No. PCT/EP2005/002284, European Patent Office, Netherlands, mailed on Aug. 2, 2005.

Co-pending U.S. Appl. No. 11/817,373, inventor Straub, A., filed Aug. 29, 2007 (Not Published).

Co-pending U.S. Appl. No. 10/597,723, inventors Dunkel, R., et al., filed May 16, 2007 (Not Published).

Co-pending U.S. Appl. No. 11/629,982, inventors Kneen, G., et al., filed Dec. 19, 2006 (Not Published).

Patent Abstracts of Japan, English language abstract of Japanese Publication No. 01-313402, published Dec. 18, 1989.

Patent Abstracts of Japan, English language abstract of Japanese Publication No. 02-040374, published Feb. 9, 1990.

Patent Abstracts of Japan, English language abstract of Japanese Publication No. 02-178259, published Jul. 11, 1990.

Patent Abstracts of Japan, English language abstract of Japanese Publication No. 08-176112, published Jul. 9, 1996.

Patent Abstracts of Japan, English language abstract of Japanese Publication No. 2001-0302605, published Oct. 31, 2001.

Dialog File 351, Accession No. 12361222, WPI English language abstract of WO 2002/08197 (listed on accompanying PTO/SB/08A as Document FP1).

Dialog File 351, Accession No. 13989121, WPI English language abstract of WO 2004/005242 (listed on accompanying PTO/SB/08A as Document FP3).

Office Action for U.S. Appl. 10/588,293 Dunkel et al., mailed Feb. 3, 2009.

International Search Report for International Application No. PCT/EP05/00629, European Patent Office, Netherlands, mailed on Jun. 6, 2005.

Lukevics, E., "Biological Activity of Nitrogen-Containing Organosilicon Compounds," *Nobel Symp.*, No. 40:435-445, Almqvist & Wiksell (1978).

Database Caplus, Chemical Abstracts Service, Accession No. 1984:5549, Hellwinkel, D., et al., 1 page (1984).

Database Caplus, Chemical Abstracts Service, Accession No. 1988:75166, Sakamoto, T., et al., 1 page (1988).

Database Caplus, Chemical Abstracts Service, Accession No. 1990:423608, Bartoli, G., 1 page (1990).

Database Caplus, Chemical Abstracts Service, Accession No. 2004:189014, Costa, M., et al., 2 pages (Apr. 2004).

International Search Report for International Application No. PCT/EP2004/012590, mailed Feb. 18, 2005, European Patent Office, Netherlands.

* cited by examiner

SILYLATED CARBOXAMIDES

The present invention relates to novel silylated carboxamides, to a plurality of processes for their preparation and for their use for controlling unwanted microorganisms.

It is already known that numerous carboxamides have fungicidal properties (cf., for example, WO 03/080628, WO 03/010149, EP-A 0 589 301, EP-A 0 545 099). The activity of these compounds is good; however, it is sometimes, for example at low application rates, unsatisfactory.

This invention now provides novel silylated carboxamides of the formula (I)

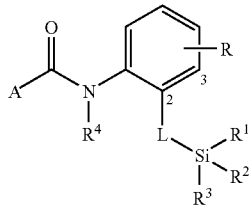

in which
R represents hydrogen, fluorine, chlorine, methyl, isopropyl, methylthio or trifluoromethyl,
L represents a direct bond or represents in each case optionally substituted straight-chain or branched alkylene (alkanediyl), alkenylene (alkenediyl) or alkynylene (alkyndiyl),
$R^1$ and $R^2$ independently of one another represent hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl,
$R^3$ represents hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-haloalkenyl, $C_2$-$C_6$-haloalkynyl, $C_3$-$C_6$-cycloalkyl, or represents in each case optionally substituted phenyl or phenylalkyl,
$R^4$ represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;
($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^5$, —CONR$^6$R$^7$ or —CH$_2$NR$^8$R$^9$,
$R^5$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^6$ and $R^7$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^6$ and $R^7$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further nonadjacent heteroatoms from the group consisting of oxygen, sulphur and NR$^{10}$,
$R^8$ and $R^9$ independently of one another, represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms,
$R^8$ and $R^9$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further nonadjacent heteroatoms from the group consisting of oxygen, sulphur and NR$^{10}$,
$R^{10}$ represents hydrogen or $C_1$-$C_6$-alkyl,
A represents the radical of the formula (A1)

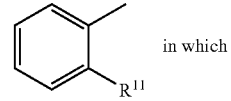

in which $R^{11}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, or A represents the radical of the formula (A2)

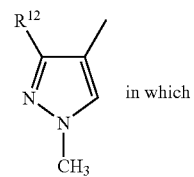

in which $R^{12}$ represents chlorine, iodine or dichloromethyl, or

A represents the radical of the formula (A3)

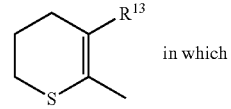

in which $R^{13}$ represents $C_1$-$C_4$-alkyl or $C_1$-$C_4$-haloalkyl having 1 to 5 halogen atoms, or A represents the radical of the formula (A4)

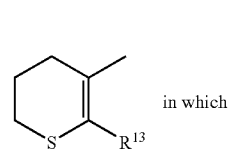

in which $R^{13}$ represents $C_1$-$C_4$-alkyl or $C_1$-$C_4$-haloalkyl having 1 to 5 halogen atoms, or
A represents the radical of the formula (A5)

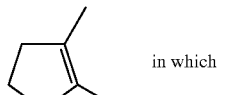
(A5)

in which $R^{14}$ represents $C_1$-$C_4$-alkyl or $C_1$-$C_4$-haloalkyl having 1 to 5 halogen atoms, or
A represents the radical of the formula (A6)

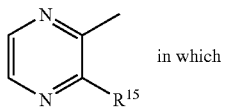
(A6)

in which $R^{15}$ represents hydrogen, halogen, $C_1$-$C_4$-alkyl or $C_1$-$C_4$-haloalkyl having 1 to 5 halogen atoms, or
A represents the radical of the formula (A7)

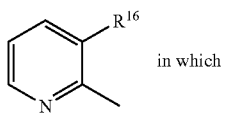
(A7)

in which $R^{16}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, or
A represents the radical of the formula (A8)

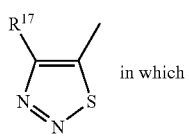
(A8)

in which $R^{17}$ represents $C_1$-$C_4$-alkyl, or
A represents the radical of the formula (A9)

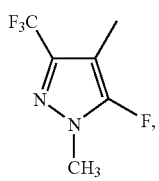
(A9)

or
A represents the radical of the formula (A10)

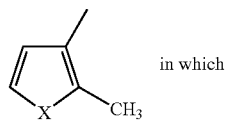
(A10)

in which

X represents O (oxygen) or S (sulphur), or
A represents the radical of the formula (A11)

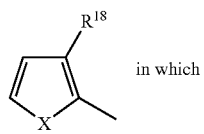
(A11)

in which

X represents O (oxygen) or S (sulphur),
$R^{18}$ represents iodine or methyl.

The compounds according to the invention can, if appropriate, be present as mixtures of various possible isomeric forms, in particular of stereoisomers, such as, for example, E and Z, threo and erythro, and also optical isomers, and, if appropriate, also of tautomers. What is claimed are both the two E and the Z isomers, and also the threo and erythro and the optical isomers, any mixtures of these isomers and the possible tautomeric forms.

Furthermore, it has been found that silylated carboxamides of the formula (I) are obtained when a) carboxylic acid derivatives of the formula (II)

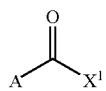
(II)

in which
$X^1$ represents halogen or hydroxyl and
A is as defined above
are reacted with amines of the formula (III)

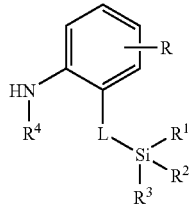
(III)

in which R, L, $R^1$, $R^2$, $R^3$ and $R^4$ are as defined above,
if appropriate in the presence of a catalyst, if appropriate in the presence of a condensing agent, if appropriate in the presence of an acid binder and if appropriate in the presence of a diluent, or
b) silylated carboxamides of the formula (I-1)

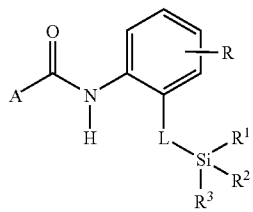
(I-1)

in which R, L, $R^1$, $R^2$, $R^3$ and A are as defined above,
are reacted with halides of the formula (VIII)

$R^{4a}$—$X^2$ (VIII)

in which

X² represents chlorine, bromine or iodine, $R^{4a}$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)R⁵, —CONR⁶R⁷ or —CH₂NR⁸R⁹, where R⁵, R⁶, R⁷, R⁸ and R⁹ are as defined in Claim 1, in the presence of a base and in the presence of a diluent.

Finally, it has been found that the novel silylated carboxamides of the formula (I) have very good microbicidal properties and can be used for controlling unwanted microorganisms both in crop protection and in the protection of materials.

The formula (I) provides a general definition of the silylated carboxamides according to the invention. Preferred radical definitions of the formulae shown above and below are given below. These definitions apply both to the end products of the formula (I) and likewise to all intermediates.

R preferably represents hydrogen.

R furthermore preferably represents fluorine, where fluorine is particularly preferably located in the 4-, 5- or 6-position, very particularly preferably in the 4- or 6-position, especially in the 4-position, of the anilide radical [cf. formula (I) above].

R furthermore preferably represents chlorine, where chlorine is particularly preferably located in the 5-position of the anilide radical [cf. formula (I) above].

R furthermore preferably represents methyl, where methyl is particularly preferably located in the 3-position of the anilide radical [cf. formula (I) above].

R furthermore preferably represents trifluoromethyl, where trifluoromethyl is particularly preferably located in the 4- or 5-position of the anilide radical [cf. formula (I) above].

L preferably represents a direct bond or represents optionally halogen-substituted straight-chain or branched $C_1$-$C_6$-alkylene, $C_2$-$C_6$-alkenylene or $C_2$-$C_6$-alkynylene.

L particularly preferably represents a direct bond or represents —CH₂—, —(CH₂)₂—, —(CH₂)₃—, —CH(Me)-, —CH(Me)CH₂—, —CH₂CH(Me)-, —CH(Me)CH(Me)-, —C(Me₂)CH₂—, —CH(Me)-(CH₂)₂—, —CH(Me)-(CH₂)₃—, —CH=CH—, —C(Me)=CH— or —C≡C—.

L very particularly preferably represents —(CH₂)₂—, —(CH₂)₃—, —CH(Me)-, —CH(Me)CH₂—, —CH(Me)-(CH₂)₂—, —CH(Me)-(CH₂)₃—, —CH=CH—, —C(Me)=CH— or —C≡C—.

R¹ and R² independently of one another preferably represent $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl.

R¹ and R² independently of one another, particularly preferably represent methyl, ethyl, methoxy, ethoxy, methoxymethyl, ethoxymethyl, methoxyethyl, ethoxyethyl, methylthiomethyl, ethylthiomethyl, methylthioethyl or ethylthioethyl.

R¹ and R² independently of one another, very particularly preferably represent methyl, methoxy, methoxymethyl or methylthiomethyl.

R¹ and R² especially preferably each represent methyl.

R³ preferably represents $C_1$-$C_6$-alkyl, $C_1$-$C_6$-alkoxy, $C_1$-$C_3$-alkoxy-$C_1$-$C_3$-alkyl, $C_1$-$C_3$-alkylthio-$C_1$-$C_3$-alkyl, $C_3$-$C_6$-cycloalkyl, phenyl or benzyl.

R³ particularly preferably represents methyl, ethyl, n- or isopropyl, n-, sec-, iso- or tert-butyl, methoxy, ethoxy, n- or isopropoxy, n-, sec-, iso- or tert-butoxy, methoxymethyl, ethoxy-methyl, methoxyethyl, ethoxyethyl, methylthiomethyl, ethylthiomethyl, methylthioethyl, ethylthioethyl, cyclopropyl, phenyl or benzyl.

R³ very particularly preferably represents methyl, ethyl, n- or isopropyl, iso- or tert-butyl, methoxy, isopropoxy, iso- or tert-butoxy, methoxymethyl, methylthiomethyl or phenyl.

R³ especially preferably represents methyl, ethyl, n- or isopropyl, iso- or tert-butyl, methoxy, isopropoxy, iso- or tert-butoxy.

R³ most preferably represents methyl.

R⁴ preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)R⁵, —CONR⁶R⁷ or —CH₂NR⁸R⁹.

R⁴ particularly preferably represents hydrogen, methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl, formyl, —CH₂—CHO, —(CH₂)₂—CHO, —CH₂—CO—CH₃, —CH₂—CO—CH₂CH₃, —CH₂—CO—CH(CH₃)₂, —(CH₂)₂—CO—CH₃, —(CH₂)₂—CO—CH₂CH₃, —(CH₂)₂—CO—CH(CH₃)₂, —CH₂—CO₂CH₃, —CH₂—CO₂CH₂CH₃, —CH₂—CO₂CH(CH₃)₂, —(CH₂)₂—CO₂CH₃, —(CH₂)₂—CO₂CH₂CH₃, —(CH₂)₂—CO₂CH(CH₃)₂, —CH₂—CO—CF₃, —CH₂—CO—CCl₃, —CH₂—CO—CH₂CF₃, —CH₂—CO—CH₂CCl₃, —(CH₂)₂—CO—CH₂CF₃, —(CH₂)₂—CO—CH₂CCl₃, —CH₂—CO₂CH₂CF₃, —CH₂—CO₂CF₂CF₃, —CH₂—CO₂CH₂CCl₃, —CH₂—CO₂CCl₂CCl₃, —(CH₂)₂—CO₂CH₂CF₃, —(CH₂)₂—CO₂CF₂CF₃, —(CH₂)₂—CO₂CH₂CCl₃, —(CH₂)₂—CO₂CCl₂CCl₃;

methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoro-methylcarbonyl, trifluoromethoxycarbonyl, or —C(=O)C(=O)R$^5$, —CONR$^6$R$^7$ or —CH$_2$NR$^8$R$^9$.

$R^4$ very particularly preferably represents hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

$R^4$ especially preferably represents hydrogen.

$R^5$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^5$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

$R^6$ and $R^7$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^6$ and $R^7$ furthermore together with the nitrogen atom to which they are attached preferably form a saturated heterocycle having 5 or 6 ring atoms which is optionally mono- to tetrasubstituted by identical or different substituents from the group consisting of halogen and $C_1$-$C_4$-alkyl, where the heterocycle may contain 1 or 2 further nonadjacent heteroatoms from the group consisting of oxygen, sulphur and NR$^{10}$.

$R^6$ and $R^7$ independently of one another, particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^6$ and $R^7$ furthermore together with the nitrogen atom to which they are attached particularly preferably form a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^{10}$.

$R^8$ and $R^9$ independently of one another, preferably represent hydrogen, $C_1$-$C_6$-alkyl, $C_3$-$C_6$-cyclo-alkyl; $C_1$-$C_4$-haloalkyl, $C_3$-$C_6$-halocycloalkyl having in each case 1 to 9 fluorine, chlorine and/or bromine atoms.

$R^8$ and $R^9$ furthermore together with the nitrogen atom to which they are attached preferably form a saturated heterocycle having 5 or 6 ring atoms which is optionally mono- or polysubstituted by identical or different substituents from the group consisting of halogen and $C_1$-$C_4$-alkyl, where the heterocycle may contain 1 or 2 further nonadjacent heteroatoms from the group consisting of oxygen, sulphur and NR$^{10}$.

$R^8$ and $R^9$ independently of one another, particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^8$ and $R^9$ furthermore together with the nitrogen atom to which they are attached particularly preferably form a saturated heterocycle from the group consisting of morpholine, thiomorpholine and piperazine, which heterocycle is optionally mono- to tetrasubstituted by identical or different substituents from the group consisting of fluorine, chlorine, bromine and methyl, where the piperazine may be substituted on the second nitrogen atom by $R^{10}$.

$R^{10}$ preferably represents hydrogen or $C_1$-$C_4$-alkyl.

$R^{10}$ particularly preferably represents hydrogen, methyl, ethyl, n- or isopropyl, n-, iso-, sec- or tert-butyl.

A preferably represents one of the radicals A1, A2, A5 or A7 shown above.

A furthermore preferably represents A6, A10 or A11.

A particularly preferably represents the radical A1.

A furthermore particularly preferably represents the radical A2.

A furthermore particularly preferably represents the radical A5.

A furthermore particularly preferably represents the radical A6.

A furthermore particularly preferably represents the radical A7.

A furthermore particularly preferably represents the radical A10.

A furthermore particularly preferably represents the radical A11.

$R^{11}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{11}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{11}$ very particularly preferably represents hydrogen, fluorine, chlorine, bromine, iodine, methyl, difluoromethyl, trifluoromethyl or trichloromethyl.

$R^{11}$ especially preferably represents chlorine, bromine, iodine, methyl, difluoromethyl or trifluoromethyl.

$R^{12}$ preferably represents iodine.

$R^{12}$ furthermore preferably represents chlorine.

$R^{12}$ furthermore preferably represents dichloromethyl.

$R^{13}$ preferably represents methyl, ethyl or $C_1$-$C_2$-haloalkyl having 1 to 5 fluorine, chlorine and/or bromine atoms.

$R^{13}$ particularly preferably represents methyl, ethyl, trifluoromethyl, difluoromethyl, difluorochloromethyl or trichloromethyl.

$R^{13}$ very particularly preferably represents methyl, trifluoromethyl, difluoromethyl or trichloro-methyl.

$R^{14}$ preferably represents methyl, ethyl or $C_1$-$C_2$-haloalkyl having 1 to 5 fluorine, chlorine and/or bromine atoms.

$R^{14}$ particularly preferably represents methyl, ethyl, trifluoromethyl, difluoromethyl, difluoro-chloromethyl or trichloromethyl.

$R^{14}$ very particularly preferably represents methyl, trifluoromethyl, difluoromethyl or trichloro-methyl.

$R^{14}$ especially preferably represents methyl or trifluoromethyl.

$R^{15}$ preferably represents hydrogen, fluorine, chlorine, bromine, methyl, ethyl or $C_1$-$C_2$-haloalkyl having 1 to 5 fluorine, chlorine and/or bromine atoms.

$R^{15}$ particularly preferably represents hydrogen, fluorine, chlorine, bromine, methyl or trifluoro-methyl.

$R^{16}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haldalkyl or $C_1$-$C_2$-haloalkoxy having in each case 1 to 5 fluorine, chlorine and/or bromine atoms.

$R^{16}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl, trichloromethyl.

$R^{16}$ very particularly preferably represents fluorine, chlorine, bromine, iodine, methyl, trifluoro-methyl, difluoromethyl or trichloromethyl.

$R^{17}$ preferably represents methyl, ethyl, n-propyl or isopropyl.

$R^{17}$ particularly preferably represents methyl or ethyl.

X preferably represents O (oxygen).

X furthermore preferably represents S (sulphur).

$R^{18}$ preferably represents iodine.

$R^{18}$ furthermore preferably represents methyl.

Emphasis is furthermore given to compounds of the formula (I-1)

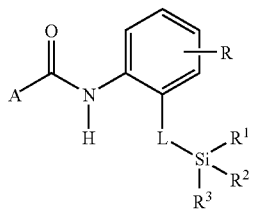

(I-1)

in which R, L, $R^1$, $R^2$, $R^3$ and A are as defined above.

Emphasis is furthermore given to compounds of the formula (I-2)

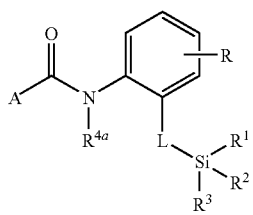

(I-2)

in which R, L, $R^1$, $R^2$, $R^3$, $R^{4a}$ and A are as defined above.

$R^{4a}$ preferably represents $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkyl-sulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^5$, —CONR$^6$R$^7$ or —CH$_2$NR$^8$R$^9$, where $R^5$, $R^6$, $R^7$, $R^8$ and $R^9$ are as defined above.

$R^{4a}$ particularly preferably represents methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CH$_2$CCl$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$—CO$_2$CF$_2$CF$_3$, —(CH$_2$)$_2$—CO$_2$CH$_2$CCl$_3$, —(CH$_2$)$_2$—CO$_2$CCl$_2$CCl$_3$;

methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl, trifluoro-methylcarbonyl, trifluoromethoxycarbonyl, or —C(=O)C(=O)$R^5$, —CONR$^6$R$^7$ or —CH$_2$NR$^8$R$^9$, where $R^5$, $R^6$, $R^7$, $R^8$ and $R^9$ are as defined above.

$R^{4a}$ very particularly preferably represents methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C(=O)CH$_3$, —C(=O)C(=O)CH$_2$OCH$_3$, —C(=O)CO$_2$CH$_3$, —C(=O)CO$_2$CH$_2$CH$_3$.

Emphasis is furthermore given to compounds of the formula (I-3)

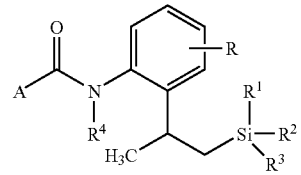

(I-3)

in which R, $R^1$, $R^2$, $R^3$, $R^4$ and A are as defined above.

Emphasis is furthermore given to compounds of the formula (I-4)

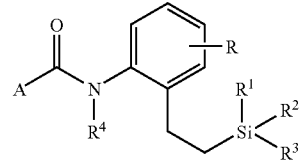

(I-4)

in which R, $R^1$, $R^2$, $R^3$, $R^4$ and A are as defined above.

Saturated or unsaturated hydrocarbon radicals, such as alkyl or alkenyl, can in each case be straight-chain or branched, as far as this is possible, including in combination with heteroatoms, such as, for example, in alkoxy.

Optionally substituted radicals may be mono- or polysubstituted, where in the case of polysubstitution the substituents can be identical or different.

Halogen-substituted radicals, such as, for example, haloalkyl, are mono- or polyhalogenated. In the case of polyhalogenation, the halogen atoms can be identical or different. Here, halogen denotes fluorine, chlorine, bromine and iodine, in particular fluorine, chlorine and bromine.

The general or preferred radical definitions or illustrations given above can be combined between the respective ranges and preferred ranges as desired. The definitions apply both to the end products and, correspondingly, to the precursors and intermediates.

Description of the Processes and Intermediates

Process (a)

Using, for example, 2-chlorobenzoyl chloride and {2-[1-methyl-2-(trimethylsilyl)ethyl]phenyl}amine as starting materials, the course of the process (a) according to the invention can be illustrated by the formula scheme below.

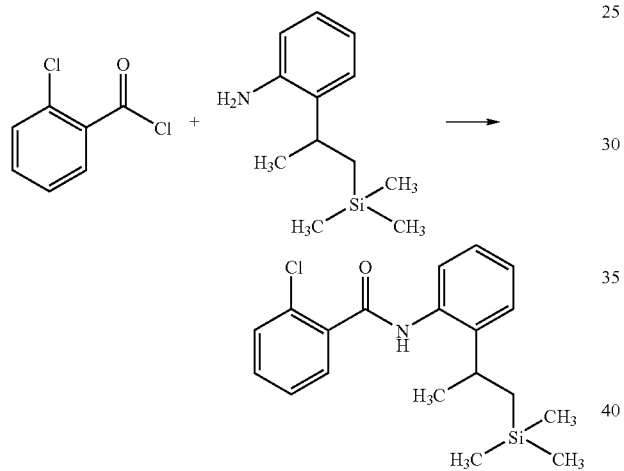

The formula (II) provides a general definition of the carboxylic acid derivatives required as starting materials for carrying out the process (a) according to the invention. In this formula (II), A preferably, particularly preferably and very particularly preferably has those meanings which have already been mentioned in connection with the description of the compounds of the formula (I) according to the invention as being preferred, particularly preferred and very particularly preferred, respectively, for these radicals. $X^1$ preferably refers to chlorine, bromine or hydroxyl.

Carboxylic acid derivatives of the formula (II) are known and/or can be obtained by known methods (cf. WO 93/11117, EP-A 0 545 099, EP-A 0 589 301, EP-A 0 589 313 and DE-A 103 25 439.0).

The formula (III) provides a general definition of the amines furthermore required as starting materials for carrying out the process (a) according to the invention. In this formula (III), R, L, $R^1$, $R^2$, $R^3$ and $R^4$ preferably, particularly preferably and very particularly preferably have those meanings which have already been mentioned in connection with the description of the compounds of the formula (I) according to the invention as being preferred, particularly preferred and very particularly preferred, respectively, for these radicals.

The amines of the formula (III) are known and/or can be obtained in a known manner (cf. WO 03/080628 and the Preparation Examples).

Amines of the formula (III) in which $R^4$ does not represent hydrogen can be obtained, for example, by reacting amines of the formula (III-a)

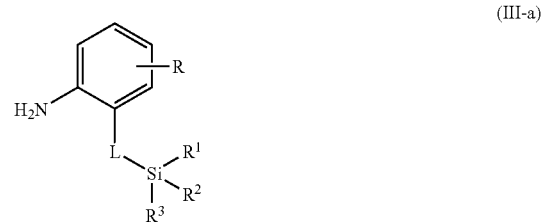

(III-a)

in which R, L, $R^1$, $R^2$ and $R^3$ are as defined above
with halides of the formula (VIII)

$$R^{4a}-X^2 \qquad (VIII)$$

in which $X^2$ and $R^{4a}$ are as defined above [the reaction conditions of the process (b) according to the invention apply correspondingly].

Process (b)

Using 2-chloro-N-{2-[1-methyl-2-(trimethylsilyl)ethyl]phenyl}benzamide and acetyl chloride as starting materials, the course of the process (b) according to the invention can be illustrated by the following formula scheme:

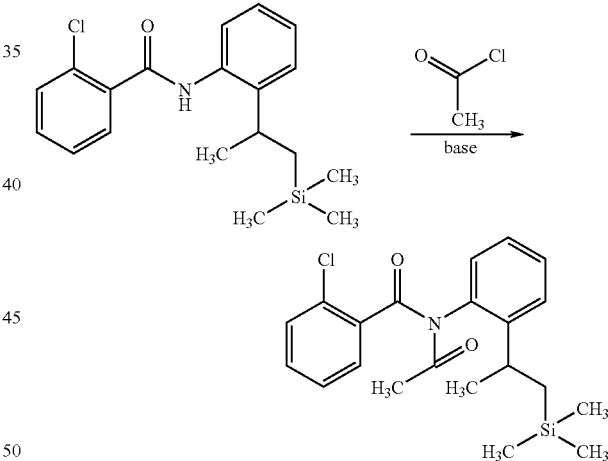

The formula (I-1) provides a general definition of the silylated carboxamides required as starting materials for carrying out the process (b) according to the invention. In this formula (I-1), R, L, $R^1$, $R^2$, $R^3$, $R^4$ and A preferably, particularly preferably and very particularly preferably have those meanings which have already been mentioned in connection with the description of the compounds of the formula (I) according to the invention as being preferred, particularly preferred and very particularly preferred, respectively, for these radicals.

The compounds of the formula (I-1) are compounds according to the invention and can be prepared by process (a).

Reaction Conditions

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl tert-amyl ether, dioxane, tetrahydrofuran, 1,2-dimethoxyethane, 1,2-diethoxyethane or anisole; amides, such as N,N-dimethylformamide, N,N-dimethylacetamide, N-methylformanilide, N-methylpyrrolidone or hexamethylphosphoric triamide. The process (a) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium acetate, potassium acetate, calcium acetate, sodium hydroxide, potassium hydroxide, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylamino-pyridine, diazabicyclooctane (DABCO), diazabicyclononene (DBN) or diazabicycloundecene (DBU).

The process (b) according to the invention is carried out in the presence of a suitable base. Suitable bases are all customary inorganic or organic bases. These preferably include alkaline earth metal or alkali metal hydrides, hydroxides, amides, alkoxides, acetates, carbonates, bicarbonates, such as, for example, sodium hydride, sodium amide, lithium diisopropylamide, sodium methoxide, sodium ethoxide, potassium tert-butoxide, sodium acetate, potassium acetate, calcium acetate, ammonium acetate, sodium hydroxide, potassium hydroxide, ammonium hydroxide, sodium carbonate, potassium carbonate, potassium bicarbonate, sodium bicarbonate or cesium carbonate; and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (a) according to the invention is, if appropriate, carried out in the presence of a suitable condensing agent. Suitable condensing agents are all condensing agents which are customarily used for such amidation reactions. Acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexyl-carbodiimide (DCC), or other customary condensing agents, such as phosphorus pentoxide, polyphosphoric acid, N,N'-carbonyldiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate may be mentioned by way of example.

The process (a) according to the invention is, if appropriate, carried out in the presence of a catalyst. Examples which may be mentioned are 4-dimethylaminopyridine, 1-hydroxybenzotriazole or dimethylformamide.

When carrying out the process (a) according to the invention, the reaction temperatures can be varied within a relatively wide range. In general, the process is carried out at temperatures of from 0° C. to 150° C., preferably at temperatures from 0° C. to 120° C., particularly preferably at temperatures from 10° C. to 80° C.

When carrying out the process (b) according to the invention, the reaction temperatures can be varied within a relatively wide range. In general the process is carried out at temperatures of from 0° C. to 150° C., preferably at temperatures of from 20° C. to 110° C.

For carrying out the process (a) according to the invention for preparing the compounds of the formula (I), in general from 0.8 to 15 mol, preferably from 0.8 to 8 mol, of amine of the formula (III) and from 1 to 3 mol of an acid binder are employed per mole of the carboxylic acid derivative of the formula (II).

For carrying out the process (b) according to the invention, in general from 0.2 to 5 mol, preferably from 0.5 to 2 mol, of a halide of the formula (a) are employed per mole of silylated carboxamide of the formula (I-1).

Unless indicated otherwise, all processes according to the invention are generally carried out under atmospheric pressure. However, it is also possible to operate under elevated or reduced pressure—in general between 0.1 bar and 10 bar.

The compounds according to the invention have potent microbicidal activity and can be employed for controlling unwanted microorganisms, such as fungi and bacteria, in crop protection and in the protection of materials.

Fungicides can be employed in crop protection for controlling *Plasmodiophoromycetes, Oomycetes, Chytridiomycetes, Zygomycetes, Ascomycetes, Basidiomycetes* and *Deuteromycetes*.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: *Drechslera,* syn: *Helminthosporium*);

*Cochliobolus* species, such as, for example, *Cochliobolus sativus* (conidia form: *Drechslera,* syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae;* and

*Pseudocercosporella* species, such as, for example, *Pseudocercosporella herpotrichoides.*

*Rhizoctonia* species, such as, for example, *Rhizoctonia solani.*

The active compounds according to the invention also show a strong invigorating action in plants. Accordingly, they are suitable for mobilizing the internal defenses of the plant against attack by unwanted microorganisms.

In the present context, plant-invigorating (resistance-inducing) compounds are to be understood as meaning substances which are capable of stimulating the defense system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned. The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be employed with particularly good results for controlling cereal diseases, such as, for example, against *Puccinia* species, and of diseases in viticulture and in the cultivation of fruit and vegetables, such as, for example, against *Botrytis, Venturia* or *Alternaria* species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (*Basidiomycetes*) and against slime organisms and algae.

Microorganisms of the following genera may be mentioned as examples:

*Alternaria,* such as *Alternaria tenuis,*

*Aspergillus,* such as *Aspergillus niger,*

*Chaetomium,* such as *Chaetomium globosum,*

*Coniophora,* such as *Coniophora puetana,*
*Lentinus,* such as *Lentinus tigrinus,*
*Penicillium,* such as *Penicillium glaucum,*
*Polyporus,* such as *Polyporus versicolor,*
*Aureobasidium,* such as *Aureobasidium pullulans,*
*Sclerophoma,* such as *Sclerophoma pityophila,*
*Trichoderma,* such as *Trichoderma viride,*
*Escherichia,* such as *Escherichia coli,*
*Pseudomonas,* such as *Pseudomonas aeruginosa,* and
*Staphylococcus,* such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxy-ethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil, fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoximmethyl; mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)

pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxa-spiro[4.5]decane-3-amine; sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella,* bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulphan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella,* cyfluthrin, cyhalothrin, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulphoton, docusat-sodium, dofenapyn, DOWCO-439, eflusilanate, emamectin, emamectin-benzoate, empenthrin (1R-isomer), endosulphan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulphothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethin, nuclear polyhedrosis viruses, kinoprene, lambda-cyhalothrin, lindane, lufenuron, malathion, mecarbam, mesulphenfos, metaldehyde, metam-sodium, methacrifos, methamidophos, *Metharhizium anisopliae, Metharhizium flavoviride,* methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus,* parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulphluramid, sulphotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii,* WL-108477, WL-40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]-octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, molds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii.* The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5,000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or proccessability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or proccessability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

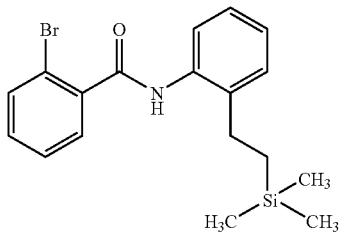

425 mg of 2-(2-trimethylsilylethyl)phenylamine (2.2 mmol) and 438 mg (2.0 mmol) of 2-bromo-benzoyl chloride were dissolved in 20 ml of acetonitrile, and 332 mg (2.4 mmol) of potassium carbonate were added. The reaction mixture was stirred at room temperature for 18 h, 20 ml of water were then added, the mixture was extracted with ethyl acetate and the extract was dried over sodium sulphate. Removal of the solvent and column-chromatographic purification on silica gel 60 (mobile phase: methylene chloride) gave 405 mg (54% of theory) of 2-bromo-N-[2-(2-trimethylsilyl-ethyl)phenyl]benzamide [log P (pH 2.3)=4.32].

The compounds of the formula (I) listed in table 1 below were also obtained analogously to example 1 and in accordance with the instructions in the general description of preparation processes (a) and (b) according to the invention:

TABLE 1

(I)

| Ex. | R | L | $R^1$ | $R^2$ | $R^3$ | $R^4$ | A | logP |
|---|---|---|---|---|---|---|---|---|
| 2 | H | *—CH(CH$_3$)—CH$_2$—# | CH$_3$ | CH$_3$ | CH$_3$ | H | 2-I-C$_6$H$_4$ | 4.67 |
| 3 | H | *—CH(CH$_3$)—CH$_2$—# | CH$_3$ | CH$_3$ | CH$_3$ | H | 2-CF$_3$-C$_6$H$_4$ | 4.63 |
| 4 | H | *—CH$_2$—CH$_2$—# | CH$_3$ | CH$_3$ | CH$_3$ | H | 2-I-C$_6$H$_4$ | 4.40 |
| 5 | H | *—CH$_2$—CH$_2$—# | CH$_3$ | CH$_3$ | CH$_3$ | H | 2-Cl-C$_6$H$_4$ | 4.29 |
| 6 | H | *—CH$_2$—CH$_2$—# | CH$_3$ | CH$_3$ | CH$_3$ | H | 2-CF$_3$-C$_6$H$_4$ | 4.37 |

TABLE 1-continued
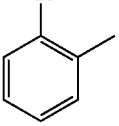
(I)
| Ex. | R | L | R¹ | R² | R³ | R⁴ | A | logP |
|---|---|---|---|---|---|---|---|---|
| 7 | H | *—CH(CH₃)—CH₂—# | CH₃ | CH₃ | CH₃ | H | 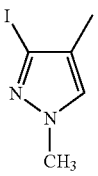 | 4.58 |
| 8 | H | *—CH₂—CH₂—# | CH₃ | CH₃ | CH₃ | H | 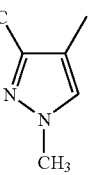 | 3.68 |
| 9 | H | *—CH₂—CH₂—# | CH₃ | CH₃ | CH₃ | H | 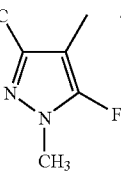 | 3.95 |
| 10 | H | *—CH₂—CH₂—# | CH₃ | CH₃ | CH₃ | H | 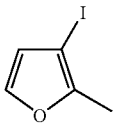 | 4.19 |
| 11 | H | *—CH(CH₃)—CH₂—# | CH₃ | CH₃ | CH₃ | H | 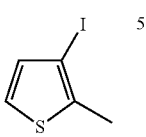 | 4.73 |
| 12 | H | *—CH(CH₃)—CH₂—# | CH₃ | CH₃ | CH₃ | H | 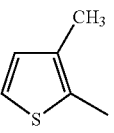 | 5.05 |
| 13 | H | *—CH₂—CH₂—# | CH₃ | CH₃ | CH₃ | H | | 4.43 |
| 14 | H | *—CH₂—CH₂—# | CH₃ | CH₃ | CH₃ | H | 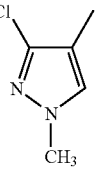 | 3.89 |

TABLE 1-continued
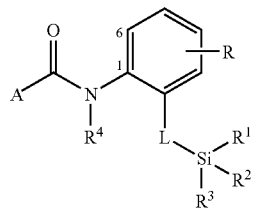
(I)
| Ex. | R | L | R¹ | R² | R³ | R⁴ | A | logP |
|---|---|---|---|---|---|---|---|---|
| 15 | H | *—CH(CH₃)—CH₂—# | CH₃ | CH₃ | CH₃ | H | 3-iodo-1,4-dimethylpyrazol-5-yl | 3.94 |
| 16 | H | *—CH₂—CH₂—# | CH₃ | CH₃ | CH₃ | H | 2,3-dimethylfuran-5-yl | 4.03 |
| 17 | H | *—CH(CH₃)—CH₂—# | CH₃ | CH₃ | CH₃ | H | 2,3-dimethylfuran-5-yl | 4.33 |
| 18 | H | *—CH=CH—# | CH₃ | CH₃ | CH₃ | H | 2-(trifluoromethyl)phenyl | 4.78 |
| 19 | H | *—CH=CH—# | CH₃ | CH₃ | CH₃ | H | 2-iodophenyl | 4.97 |
| 20 | H | *—CH=CH—# | CH₃ | CH₃ | CH₃ | H | 2-chlorophenyl | 4.96 |
| 21 | H | *—CH=CH—# | CH₃ | CH₃ | CH₃ | H | 2-bromophenyl | 4.93 |
| 22 | 4-F | *—CH(CH₃)—CH₂—# | CH₃ | CH₃ | CH₃ | H | 2-(trifluoromethyl)phenyl | 4.61 |

TABLE 1-continued

(I)

| Ex. | R | L | R¹ | R² | R³ | R⁴ | A | logP |
|---|---|---|---|---|---|---|---|---|
| 23 | 4-F | *—CH(CH₃)—CH₂—# | CH₃ | CH₃ | CH₃ | H | 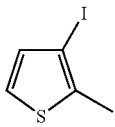 | 4.64 |
| 24 | H | *—CH₂—CH₂—# | CH₃ | CH₃ | CH₃ | H | 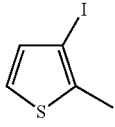 | 4.85 |
| 25 | 4-F | *—CH₂—CH₂—# | CH₃ | CH₃ | CH₃ | H | 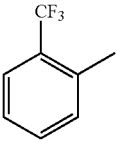 | 4.79 |
| 26 | 4-F | *—CH₂—CH₂—# | CH₃ | CH₃ | CH₃ | H | 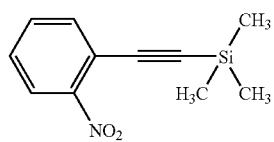 | 4.39 |

The bond marked with the asterisk (*) is attached to the aniline radical, the bond marked with the hash (#) mark is attached to the silicon substituent.

Preparation of Starting Materials of the Formula (III)

Example (III-1)

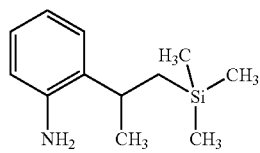

17.7 g of aniline (0.19 mol), 50 g of allyltrimethylsilane (0.44 mol), 1.5 g of aluminum trichloride (0.01 mol) and 0.5 g of aluminum powder (0.02 mol) were mixed and stirred in an autoclave at 255° C. for 10 h. After cooling to room temperature, initially 100 ml of toluene and then 40 ml of a 40% strength solution of NaOH in water and 100 ml of water were added, and the mixture was stirred at 35° C. for 15 min. After cooling, the mixture was extracted with toluene, the extract was washed with water and dried over potassium carbonate and the solvent was removed under reduced pressure. Distillation (55° C.-60° C., 0.08 mbar) gave 1.4 g of 2-(1-methyl-2-trimethylsilylethyl)phenylamine [log P (pH 2.3)=3.05].

Example (III-2)

Step 1

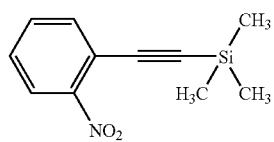

4 g (20 mmol) of ortho-bromonitrobenzene, 842 mg (1.2 mmol) of bis(triphenyl-phosphine)palladium(II) chloride and 230 mg (1.2 mmol) of copper(I) iodide were, under argon, initially charged in 40 ml of triethylamine. At room temperature, 2.95 g (30 mmol) of trimethylsilylacetylene were then added dropwise over a period of 10 min, and the mixture was stirred at room temperature for 2 days. The reaction mixture was poured into 50 ml of water and extracted three times with in each case 50 ml of diethyl ether, and the extracts were dried over sodium sulphate and concentrated. Column-chromatographic purification on silica gel 60 (mobile phase: cyclohexane/ethyl acetate 3:1) gave 4.2 g (96% of theory) of trimethyl-(2-nitrophenyl-ethynyl)silane [log P (pH 2.3)=4.12].

Step 2

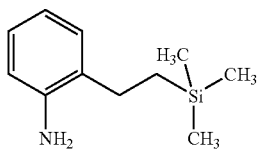

10.9 g (50 mmol) of trimethyl-(2-nitrophenylethynyl)silane were dissolved in 200 ml of methanol, and 0.5 g of palladium-on-carbon (5%) were added. The mixture was then hydrogenated in an autoclave at 4 bar for 12 h. Removal of the solvent and column-chromatographic purification on silica gel 60 (mobile phase: methylene chloride) gave 4.1 g of 2-(2-trimethylsilylethyl)phenylamine [log P (pH 2.3)=2.58].

The given log P values were determined in accordance with EEC Directive 79/831 Annex V.A8 by HPLC (High Performance Liquid Chromatography) on a reverse-phase column (C 18). Temperature: 43° C.

Mobile phases for the determination in the acidic range (pH 2.3): 0.1% aqueous phosphoric acid, acetonitrile; linear gradient from 10% acetonitrile to 90% acetonitrile.

Calibration was carried out using unbranched alkan-2-ones (3 to 16 carbon atoms) with known log P values (determination of the log P values by the retention times using linear interpolation between two successive alkanones).

The lambda-max values were determined in the maxima of the chromatographic signals using the UV spectra from 200 nm to 400 nm.

USE EXAMPLES

Example A

Venturia Test (Apple)/Protective

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple pathogen *Venturia inaequalis* and then remain in an incubation cabin at about 20° C. and 100% relative atmospheric humidity for one day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE A

Venturia test (apple)/protective

| Active compound according to the invention | Application rate of active compound in g/ha | Efficacy in % |
|---|---|---|
| 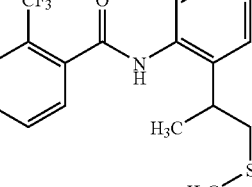 | 100 | 99 |
| 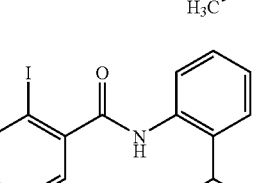 | 100 | 100 |
| 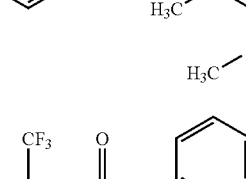 | 100 | 84 |
| 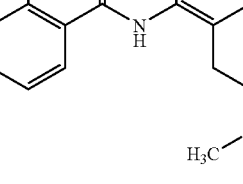 | 100 | 87 |
| 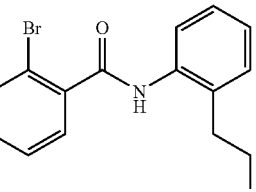 | 100 | 100 |
| 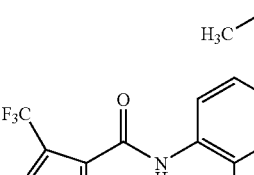 | 100 | 100 |

TABLE A-continued

Venturia test (apple)/protective

| Active compound according to the invention | Application rate of active compound in g/ha | Efficacy in % |
|---|---|---|
| 3-methyl-thiophene-2-carboxamide with 2-(2-(trimethylsilyl)ethyl)phenyl | 100 | 100 |
| 3-iodo-thiophene-2-carboxamide with 4-fluoro-2-(2-methyl-3-(trimethylsilyl)propyl)phenyl | 100 | 100 |
| 3-iodo-furan-2-carboxamide with 2-(2-methyl-3-(trimethylsilyl)propyl)phenyl | 100 | 100 |
| 3-iodo-thiophene-2-carboxamide with 2-(2-methyl-3-(trimethylsilyl)propyl)phenyl | 100 | 100 |
| 3-iodo-1-methyl-pyrazole-4-carboxamide with 2-(2-methyl-3-(trimethylsilyl)propyl)phenyl | 100 | 99 |

Example B

Sphaerotheca Test (Cucumber)/Protective

| | |
|---|---|
| Solvent: | 49 parts by weight of N,N-dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the preparation of active compound at the stated application rate. One day after the treatment, the plants are inoculated with a spore suspension of *Sphaerotheca fuliginea*. The plants are then placed in a greenhouse at 70% relative atmospheric humidity and a temperature of 23° C.

Evaluation is carried out 7 days after the inoculation. 0% means an efficacy which corresponds to that of the control, whereas an efficacy of 100% means that no infection is observed.

TABLE B

*Sphaerotheca* test (cucumber)/protective

| Active compound according to the invention | Application rate of active compound in g/ha | Efficacy in % |
|---|---|---|
| 2-(trifluoromethyl)benzamide with 2-(2-methyl-3-(trimethylsilyl)propyl)phenyl | 750 | 100 |
| 2-iodo-benzamide with 2-(2-methyl-3-(trimethylsilyl)propyl)phenyl | 750 | 100 |
| 2-bromo-benzamide with 2-(2-(trimethylsilyl)ethyl)phenyl | 750 | 100 |

Example C

Puccinia Test (Wheat)/Protective

| | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondite*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out ten days after the inoculation. 0% means an efficacy which corresponds to that of the control, whereas an efficacy of 100% means that no infection is observed.

TABLE C

*Puccinia* test (wheat)/protective

| Active compound according to the invention | Application rate of active compound in g/ha | Efficacy in % |
|---|---|---|
| (structure) | 500 | 93 |
| (structure) | 500 | 100 |
| (structure) | 500 | 100 |
| (structure) | 500 | 100 |
| (structure) | 500 | 100 |
| (structure) | 500 | 100 |

TABLE C-continued

Puccinia test (wheat)/protective

| Active compound according to the invention | Application rate of active compound in g/ha | Efficacy in % |
|---|---|---|
| 3-methylthiophene-2-carboxamide, N-[2-(2-(dimethylsilyl)ethyl)phenyl]- | 500 | 100 |
| 3-iodothiophene-2-carboxamide, N-[2-(2-(dimethylsilyl)ethyl)phenyl]- | 500 | 100 |
| 3-iodothiophene-2-carboxamide, N-[4-fluoro-2-(2-(dimethylsilyl)ethyl)phenyl]- | 500 | 100 |
| 3-iodofuran-2-carboxamide, N-[2-(1-methyl-2-(dimethylsilyl)ethyl)phenyl]- | 500 | 100 |
| 3-iodothiophene-2-carboxamide, N-[2-(1-methyl-2-(dimethylsilyl)ethyl)phenyl]- | 500 | 100 |
| 2-bromobenzamide, N-[2-(1-methyl-2-(dimethylsilyl)ethyl)phenyl]- | 500 | 100 |
| 3-iodo-1-methylpyrazole-4-carboxamide, N-[2-(1-methyl-2-(dimethylsilyl)ethyl)phenyl]- | 500 | 100 |

The invention claimed is:
1. Silylated carboxamides of the formula (I)

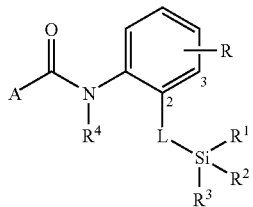

(I)

in which
R is hydrogen, fluorine, chlorine, methyl, isopropyl, methylthio or trifluoro-methyl,
L is a direct bond or is in each case optionally substituted straight-chain or branched alkylene (alkanediyl), alkenylene (alkenediyl) or alkynylene (alkyndiyl),
$R^1$ and $R^2$ independently of one another are hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl or $C_1$-$C_6$-haloalkyl,
$R^3$ is hydrogen, $C_1$-$C_8$-alkyl, $C_1$-$C_8$-alkoxy, $C_1$-$C_4$-alkoxy-$C_1$-$C_4$-alkyl, $C_1$-$C_4$-alkylthio-$C_1$-$C_4$-alkyl, $C_2$-$C_8$-alkenyl, $C_2$-$C_8$-alkynyl, $C_1$-$C_6$-haloalkyl, $C_2$-$C_6$-halo-alkenyl, $C_2$-$C_6$-haloalkynyl, $C_3$-$C_6$-cycloalkyl, or is in each case optionally substituted phenyl or phenylalkyl,
$R^4$ is hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocyclo-alkyl)carbonyl having in each case 1 to 9 fluorine, chlorine and/or bromine atoms; or —C(=O)C(=O)$R^5$, —CONR$^6$R$^7$ or —CH$_2$NR$^8$R$^9$,
$R^5$ is hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^6$ and $R^7$ independently of one another each are hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^6$ and $R^7$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^{10}$,
$R^8$ and $R^9$ independently of one another, are hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms,
$R^8$ and $R^9$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^{10}$,
$R^{10}$ is hydrogen or $C_{-1}$-$C_6$-alkyl,
A is the radical of the formula (A2)

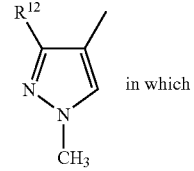

(A2)

in which $R^{12}$ is chlorine or iodine.

2. A silylated caboxamide of the formula (I) of claim 1, wherein
R is hydrogen, fluorine, chlorine, methyl or trifluoromethyl,
L is a direct bond or is in each case optionally halogen-substituted straight-chain or branched $C_1$-$C_6$-alkylene, $C_2$-$C_6$-alkenylene or $C_2$-$C^6$-alkynylene,
$R^1$ and $R^2$ independently of one another are $C_1$-$C_6$-alkyl, $C_1$-$C_6$-alkoxy, $C_1$-$C_3$-alkoxy-$C_1$-$C_3$-alkyl or $C_1$-$C_3$-alkylthio-$C_1$-$C_3$-alkyl,
$R^3$ is $C_1$-$C_6$-alkyl, $C_1$-$C_6$-alkoxy, $C_1$-$C_3$-alkoxy-$C_1$-$C_3$-alkyl, $C_1$-$C_3$-alkylthio -$C_1$-$C_3$-alkyl, $C_3$-$C_6$-cycloalkyl, phenyl or benzyl,
$R^4$ is hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo -($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halo-cycloalkyl)carbonyl having in each case 1 to 9 fluorine, chlorine and/or bromine atoms, or —C(=O)C(=O)$R^5$, —CONR$^6$R$^7$ or —CH$_2$NR$^8$R$^9$,
$R^5$ is hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms,
$R^6$ and $R^7$ independently of one another each are hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms,
$R^6$ and $R^7$ furthermore together with the nitrogen atom to which they are attached form a saturated heterocycle having 5 or 6 ring atoms which is optionally mono- to tetrasubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^{10}$,
$R^8$ and $R^9$ independently of one another are hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms, $R^8$ and $R^9$ furthermore together with the nitrogen atom to which they are attached form a saturated heterocycle having 5 or 6 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and $NR^{10}$, $R^{10}$ is hydrogen or $C_1$-$C_4$-alkyl, A is the radical of the formula (A2)

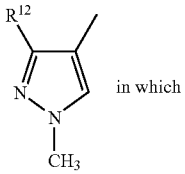
(A2)

in which $R^{12}$ is chlorine or iodine.

3. A process for preparing silylated carboxamides of the formula (I) according to claim 1, comprising reacting a) carboxylic acid derivatives of the formula (II)

(II)

in which $X^1$ is halogen or hydroxyl and

A is as defined in claim 1 are reacted with amines of the formula (III)

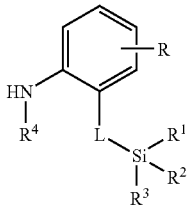
(III)

in which R, L, $R^1$, $R^2$, $R^3$ and $R^4$ are as defined in claim 1, optionally in the presence of a catalyst, optionally in the presence of a condensing agent, optionally in the presence of an acid binder and optionally in the presence of a diluent, or b) silylated carboxamides of the formula (I-1)

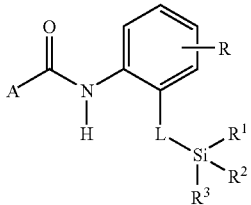
(I-1)

in which R, L, $R^1$, $R^2$, $R^3$ and A are as defined in claim 1, are reacted with halides of the formula (VIII)

$$R^{4a}-X^2 \quad (VIII)$$

in which $X^2$ is chlorine, bromine or iodine, $R^{4a}$ is $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkyl-thio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^5$, —CONR$^6$R$^7$ or —CH$_2$NR$^8$R$^9$, where $R^5$, $R^6$, R 7, $R^8$ and $R^9$ are as defined in claim 1, in the presence of a base and in the presence of a diluent.

4. A composition, comprising at least one silylated carboxamide of the formula (I) according to claim 1, in addition to extenders and/or surfactants.

5. A method of controlling fungi in the protection of crops or industrial materials comprising applying the composition of claim 4 to said fungi or their habitat, or both.

6. A method for controlling fungi in the protection of crops or industrial materials, comprising applying the silylated carboxamides of the formula (I) according to claim 1 to said fungi, their habitats, or both.

7. A process for preparing a composition comprising mixing the silylated carboxamides of the formula (I) according to claim 1 with extenders, surfactants, or both.

8. The method of claim 5 wherein said fungi is selected from the group consisting of *Plasmodiophoromycetes, Oomycetes, Chytridiomycetes, Zygomycetes, Ascomycetes, Basidiomycetes*, and *Deuteromycetes*.

9. The method of claim 5 wherein said fungi is selected from the group consisting of *Basidiomycetes, Alternaria, Aspergillus, Chaetomium, Coniophora, Lentinus, Penicillium, Polyporus, Aureobasidium, Sclerophoma*, and *Trichoderma*.

10. The method of claim 5 wherein said fungi is selected from the group consisting of Puccinia, Sphaerotheca and Venturia.

11. The method of claim 5 wherein said fungi is selected from the group consisting of *Puccinia recondita, Sphaerotheca fuliginia* and *Venturia inaequalis*.

12. The method of claim 6 wherein said fungi is selected from the group consisting of *Plasmodiophoromycetes, Oomycetes, Chytridiomycetes, Zygomycetes, Ascomycetes, Basidiomycetes*, and *Deuteromycetes*.

13. The method of claim 6 wherein said fungi is selected from the group consisting of *Basidiomycetes, Alternaria, Aspergillus , Chaetomium, Coniophora, Lentinus, Penicillium, Polyporus, Aureobasidium, Sclerophoma, and Trichoderma*.

14. The method of claim 6 wherein said fungi is selected from the group consisting of *Puccinia, Sphaerotheca and Venturia*.

15. The method of claim 6 wherein said fungi is selected from the group consisting of *Puccinia recondita, Sphaerotheca fuliginia* and *Venturia inaequalis*.

* * * * *